United States Patent [19]
Yasuda et al.

[11] 3,933,783
[45] Jan. 20, 1976

[54] FORMATION OF PEPTIDE BONDS IN THE PRESENCE OF ISONITRILES

[75] Inventors: Naohiko Yasuda, Kawasaki; Yasuo Ariyoshi; Koji Toi, both of Yokohama, all of Japan

[73] Assignee: Ajinomoto Co., Inc., Tokyo, Japan

[22] Filed: Dec. 9, 1974

[21] Appl. No.: 530,494

Related U.S. Application Data

[62] Division of Ser. No. 317,921, Dec. 26, 1972, Pat. No. 3,872,099.

[30] Foreign Application Priority Data

Dec. 27, 1971 Japan.................................. 46-1997
Nov. 27, 1972 Japan.............................. 47-115332

[52] U.S. Cl........................................ 260/112.5 R
[51] Int. Cl.².................................... C07C 103/52
[58] Field of Search................................. 260/112.5

[56] References Cited
UNITED STATES PATENTS
3,721,662   3/1973   Fujino et al...................... 260/112.5

OTHER PUBLICATIONS
Yasumoto et al.: Chem. Abstr., 68:60069t(1968).
Gokel et al.: "Isonitrile Chemistry," I. Ugi, ed., Academic Press, New York, 1971, pp. 20–22.

Primary Examiner—Elbert L. Roberts
Assistant Examiner—Reginald J. Suyat
Attorney, Agent, or Firm—Hans Berman

[57]  ABSTRACT

Amino acids having masked amino groups react with amino acids having masked carboxyl groups to form peptide derivatives in good yields if the reaction medium contains an isonitrile. Isonitriles also are effective in causing condensation of amino acids having masked amino groups with compounds having active hydroxyl groups to the corresponding amino acid esters. The yields of the first-mentioned reaction are enhanced if the reaction mixture additionally contains one of the compounds having active hydroxyl groups. Both the peptide derivatives and the amino acid esters of the compounds having active hydroxyl groups are useful for peptide synthesis.

11 Claims, No Drawings

FORMATION OF PEPTIDE BONDS IN THE PRESENCE OF ISONITRILES

This application is a division of the copending application Ser. No. 317,921, filed Dec. 26, 1972, and now U.S. Pat. No. 3,872,099.

This invention relates to peptide synthesis, and particularly to the production of active esters of amino acids and oligopeptides suitable for N-acylation of other amino acids or peptides and for the formation or extension of a peptide chain resulting from the acylation.

Such active esters were prepared heretofore from amino acids and oligopeptides by condensation in the presence of an N,N'-disubstituted carbodiimide. The latter forms substantial amounts of urea derivatives which are not readily removed from the desired product and are reconverted to the carbodiimide derivative only with much difficulty when they can be isolated from the reaction mixture.

It has now been found that isonitriles generally are as effective as the known carbodiimide derivatives in promoting the condensation of amino acids and oligopeptides to active esters, that the yields of the desired products are better, and that any by-products which may be formed are readily separated from the desired active ester.

The invention provides a method in which an amino acid having a masked amino group and an available carboxyl group, hereinafter also referred to as an N-protected amino acid, is contacted with at least one member of the group consisting of a compound having an active hydroxyl group and an amino acid having a masked carboxyl group and an available amino group, hereinafter also referred to as a carboxyl-protected amino acid, in a liquid reaction system in the presence of an isonitrile until a peptide or an ester of an amino acid derivative active for peptide synthesis is formed, whereupon the last-mentioned peptide or ester is recovered.

The term "amino acid," as employed in this specification and the appended claims, embraces oligopeptides having the free and available amino and carboxyl groups of an amino acid unless specifically stated otherwise, and constituted by more than one amino acid unit connected by peptide linkage.

The starting materials having protected amino or carboxyl groups may be derived in a conventional manner from any amino acid or oligopeptide, and the many masking groups in common usage in peptide chemistry may be employed in preparing starting materials for the reaction of the invention. Suitable masking groups for amino groups thus include, but are not limited to, carbobenzoxy, tert-butyloxycarbonyl, phthalyl, formyl, tosyl, and o-nitrophenylsulfenyl. The carboxyl groups may be masked by conversion to esters, amides, or salts. The lower alkyl esters, such as the methyl, ethyl, tert-butyl esters, and benzyl esters are preferred because of their convenient accessibility and generally relatively low cost, but the potassium and sodium salts and amides also may be employed.

If the amino acids and peptides employed as starting materials have secondary, reactive, functional groups, it is often desirable to mask them also to avoid the formation of byproducts. Such secondary functional groups are present, for example, in basic amino acids having more than one amino group, such as lysine and arginine, acidic amino acids having more than one carboxyl group such as aspartic and glutamic acid, amino acids having mercapto groups such as cysteine, and the peptides containing units of such polyfunctional amino acids.

The compounds having active hydroxyl groups that may be combined with N-protected amino acids in the presence of an isonitrile to form esters are a broad class, and many have been enumerated in a recent paper (J. Synthetic Organic Chemistry, Japan, 29 [1971]27). The compounds listed in the paper are useful in this invention without exception. They include p-nitrophenol, chlorinated phenols including the tri- and tetrachlorophenols, N-hydroxysuccinimide, N-hydroxybenzotriazole, 8-hydroxyquinoline, and N-hydroxypiperidine.

The mole ratio of the reactants in the method of this invention is not critical. They usually react in equimolar amounts, and any excess present may remain unchanged. It is normally most economical to prpeare the reaction mixture from equimolar amounts of the amino acid having a masked amino group and the amino acid having a masked carboxyl group and/or the compound having an active hydroxyl group. In the reaction of an N-protected amino acid with a carboxy-protected amino acid, better yields are achieved when the former is employed in slight molar excess.

The NC group is the active moiety in the isonitriles employed as condensing agents, and any isonitrile free from obviously interfering functional groups is suitable. Alkyl, alkenyl, aryl, and aralkyl isonitriles are preferred. They may have functional substituents which do not interfere with the desired reaction, such as halogen, nitro, or ester groups. Conveniently available condensation agents of the invention thus include isopropyl isonitrile, n-butyl isonitrile, tert-butyl isonitrile, phenyl isonitrile, and benzyl isonitrile, also allyl isonitrile. They should be present in an amount of at least one mole per mole of the amino acid having a masked amino group to be fully effective, and incomplete conversion of the principal reactants occurs in the presence of a smaller amount of condensing agent. An excess of the isonitrile over the minimum amount is not normally harmful though wasteful if it exceeds 100 percent.

The reaction is carried out in a liquid medium, and the mixture of reactants and of the isonitrile may constitute such a medium, an excess of the isonitrile providing improved liquidity. The reaction also takes place in aqueous solution, but it is preferably carried out in a suitable amount of inert organic solvent such as methylene chloride, chloroform, ethylene dichloride, ethyl ether, tetrahydrofuran, dioxane, ethyl acetate, acetonitrile, or dimethylformamide.

The sequence in which the ingredients of the reaction mixture are combined is not critical. In the reaction of an N-protected amino acid with a carboxyl-protected amino acid, better yields are achieved when the carboxyl-protected amino acid is added last, or even in several spaced batches while the reaction proceeds.

The reaction occurs over the wide range of temperatures in which the reaction system is liquid, and the time required to achieve a desired conversion rate is normally inversely proportional to the temperature. The reaction rates below about 10°C are extremely sluggish, and decomposition may occur at temperatures above about 80°C. However, neither limit is absolute in the sense that none of the desired products could be formed below 10° or above 80°C. If optically active starting materials are to be converted to optically active end products, thermal racemization is to be avoided in a well known manner by keeping the reaction temperature below 70°C. A reaction temperature of about 40° to 60°C usually offers the best combination of adequate reaction rate and minimal decomposition and racemization. The reaction time for optimum yield may vary between a few hours and 100 hours, depending on the nature of the reactants and other process variables. The esters of N-protected amino acids with compounds having active hydroxyl groups are generally formed quicker than the peptides with carboxyl-protected amino acids.

For reasons not yet fully elucidated, the reaction between an N-protected amino acid and a carboxyl-protected amino acid to the corresponding peptide in the presence of an isonitrile condensing agent proceeds at higher yield if one of the afore-mentioned compounds having an active hydroxyl group is simultaneously present in the reaction mixture, and significant amounts of esters of the N-protected amino acid with the compound having an active hydroxyl group are not found in the ultimate reaction mixture.

The same peptide can be formed, of course, by first reacting the N-protected amino acid with the compound having an active hydroxyl group to produce the expected ester, then isolating the ester, and reacting the same with the carboxyl-protected amino acid. It appears plausible that the ester of the N-protected amino acid with the compound having an active hydroxyl group is formed first as an intermediate which thereafter reacts with the carboxyl-protected amino acid. Some support for this assumption is found in the fact that, contrary to the direct direction between the N-protected and carboxyl-protected amino acids in the presence of an isonitrile, the yield is not effected by the timing in the addition of the carboxyl-protected amino acid. The latter may be present in its entirety at the beginning of the reaction. Equimolecular amounts of the N-protected and carboxyl-protected amino acids may be employed.

During the formation of an ester from a compound having an active hydroxyl compound and an N-protected amino acid in the presence of an isonitrile, N-substituted formamides are formed as by-products. Similar by-products are also formed in the absence of the compounds having active hydroxyl groups, and are readily removed from the reaction mixture prior to recovery of the desired peptide derivative. The formamide derivatives resulting from the use of n-propyl, i-propyl, or tert-butyl isonitrile are very volatile in a vacuum and may be distilled off, leaving a pure reaction product. Dehydrating agents, such as phosgene and phosphorus oxychloride again convert the N-substituted formamides to the isonitriles for return to the process.

The following examples are further illustrative of the invention. The compounds formed were identified by their elementary analysis, as listed below, and their structure verified by infrared and nuclear magnetic resonance spectra.

EXAMPLE 1

A solution of 6.0 g (20 millimole) N-carbobenzoxy-L-phenylalanine and 2.1 g (30 millimole) isopropyl isonitrile (isopropyl isocyanide, 2-isocyanopropane, or isopropylcarbylamine) in 40 ml methylene chloride was refluxed at 45°–50°C. A solution of 2.06 g (20 millimole) glycine ethyl ester in 40 ml methylene chloride was divided into three equal portions which were added to the refluxing material after 3, 16, and 21 hours respectively. Refluxing was continued for six hours after the last addition.

The reaction mixture was stripped of solvent, N-isopropylformamide, and unreacted isopropyl isonitrile by vacuum distillation, and the residue was dissolved in 150 ml ethyl acetate. The solution was washed sequentially with 1-N hydrochloric acid, 4% sodium bicarbonate solution, and water, dried with desiccated sodium sulfate, and evaporated to dryness. The residue was crystallized from ethyl acetate and petroleum ether, and 4.7 g N-carbobenzoxy-L-phenylalanyl-glycine ethyl ester was obtained (61 percent yield).

When recrystallized from ethyl acetate and petroleum ether, it melted at 105°–107°C and had a specific rotation of $[\alpha]_D^{25} = -17.1°$ (C = 2.1, in ethanol).

Calculated for $C_{21}H_{24}O_5N_2$: 65.61% C; 6.29% H; 7.29% N. Found: 65.88% C; 6.46% H; 7.23% N.

EXAMPLE 2

The procedure of Example 1 was repeated, using different isonitriles in partly different solvents at partly different temperatures for partly different reaction periods. The molar amounts of the several reactants and the volumes of solvents remained unchanged. The modified conditions and the yields of N-carbobenzoxy-L-phenylalanyl-glycine ethyl ester are indicated below.

N-Propyl isonitrile in methylene chloride for 70 hours at 20°–25°C produced a yield of 67 percent.

Phenyl isonitrile in chloroform at 40°C for 28 hours gave a yield of 64 percent.

Benzyl isonitrile in dioxane at 50°–60°C gave a 51 percent yield in 20 hours.

Ethoxycarbonylmethyl isonitrile in acetonitrile produced a yield of 63 percent in 40 hours at 20°–25°C.

EXAMPLE 3

A solution of 12 g (48 mM) N-carbobenzoxy-L-proline in 30 ml chloroform was mixed with a solution of 7.3 g (40 mM) L-leucine methyl ester hydrochloride in 50 ml chloroform neutralized with 4 g (40 mM) triethylamine. 3.3 g (48 mM) n-Propyl isonitrile was added to the mixture which was then held at 40°–50°C for 45 hours.

The reaction mixture was eveporated in a vacuum, and the residue was taken up in 300 ml ethyl acetate. Undissolved triethylamine hydrochloride was filtered off, and the filtrate was washed sequentially with dilute hydrochloric acid, sodium bicarbonate solution, and water, and dried over desiccated sodium sulfate as in Example 1. Upon evaporation of the solvent and crystallization of the residue from ethyl acetate and petroleum ether, 9.1 g N-carbobenzoxy-L-prolyl-L-leucine methyl ester was obtained (61 percent yield, based on the L-leucine methyl ester hydrochloride). When recrystallized from ethyl acetate and petroleum ether, the compound melted at 73.5°–75.5°C and had a specific rotation of $[\alpha]_D^{25} = -68°$ (C = 1.5, in ethanol).

Calculated for $C_{20}H_{28}O_5N_2$: 63.81% C; 7.50% H; 7.44% N. Found: 63.70% C; 7.35% H; 7.49% N.

EXAMPLE 4

A solution of 3.9 g (20 mM) N-formyl-L-phenylalanine, 2.5 g (24 mM) glycine ethyl ester, and 1.7 g (20 mM) tert-butyl isonitrile in 30 ml dioxane was heated at 40°–50°C for 28 hours. It was then evaporated to dryness, and the residue was dissolved in 300 ml methylene chloride. The solution was washed as in the preceding examples, dried, and evaporated. The residue was crystallized from carbon tetrachloride and petroleum ether to produce 3.1 g N-formyl-L-phenylalanyl-glycine ethyl ester (48 percent yield based on the glycine ethyl ester).

When recrystallized from the same solvents, the compound melted at 126.5°–129.5°C and had a specific rotation of $[\alpha]_D^{25} = 4.0°$ (C = 2.1, in ethanol).

Calculated for $C_{14}H_{18}O_4N_2$: 60.42% C; 6.52% H; 10.07% N. Found: 60.28% C, 6.60% H; 10.13% N.

EXAMPLE 5

20 Millimole $N^\alpha$, $N^\epsilon$-dicarbobenzoxy-L-lysine and 30 mM isopropyl isonitrile was dissolved in 20 ml methylene chloride, and the mixture was kept at ambient temperature of about 20° C. A solution of 20 millimole glycine ethyl ester in enough ethylene chloride to make 20 ml was divided into three equal portions which were added to the first solution when the latter was 4, 21, and 28 hours old respectively. The reaction mixture thereafter was left to stand for another 20 hours.

It was then evaporated to dryness in a vaccum, the residue was taken up in 150 ml ethyl acetate, and the ethyl acetate solution was washed, dried, and evaporated as above. The residue was crystallized from ethyl acetate and petroleum ether, and $N^\alpha$, $N^\epsilon$-dicarbobenzoxy-L-lysyl-glycine ethyl ester was obtained in a yield of 72 percent.

Equivalent amounts of N-protected amino acids were reacted with carboxyl-protected amino acids or peptides in the same manner to produce N-protected peptide esters with the yields indicated below:

N-Carbobenzoxy-L-aspartic acid β-benzyl ester and L-phenylalanine methyl ester produced N-carbobenzoxy-β-benzyl-L-aspartyl-L-phenylalanine methyl ester (58 percent yield).

N-Carbobenzoxy-L-alanine and L-phenylalanine methyl ester gave N-carbobenzoxy-L-alanyl-L-phenylalanine methyl ester (70 percent yield).

N-Carbobenzoxy-glycine Carbobenzoxy-glycine and L-phenylalanyl-glycine ethyl ester were converted to N-carbobenzoxy-glycyl-L-phenylalanyl-glycine ethyl ester (68 percent yield).

EXAMPLE 6

A solution of 4.18 g (20 mM) N-carbobenzoxy-glycine, 2.3 g (20 mM) N-hydroxysuccinimide, and 2.0 g (30 mM) isopropyl isonitrile in 70 ml ethyl acetate was heated at 65°C for 30 hours, whereupon the solvent was evaporated, and the residue was triturated with ether until a powder of N-carbobenzoxy-glycine N-hydroxysuccinimide ester was formed. The powder was separated from a mother liquor and washed with petroleum ether. The mother liquor and washings were combined and cooled whereby more of the same compound was precipitated in crystalline form and filtered off. The total yield was 4.95 g (81 percent). When recrystallized from methylene chloride and petroleum ether, the compound melted at 110°–112°C.

Calculated for $C_{14}H_{14}O_6H_2$: 55.01% C; 4.66% H; 8.80% N. Found: 54.90% C; 4.61% H; 9.15% N.

N-hydroxysuccinimide formed the expected esters with equivalent amounts of other N-carbobenzoxyamino acids in the presence of 1.5 mole isonitrile under partly modified conditions in good yields.

The ester with N-carbobenzoxy-L-proline was obtained in the presence of N-propyl isonitrile in methylene chloride at 40°C in 42 hours in a yield of 41%, melted at 95°–87°C and had a specific rotation of $[\alpha]_D^{25} = -55°$ (C = 2, in dioxane).

The ester with N-carbobenzoxy-L-valine was formed in chloroform with tert-butyl isonitrile at 70°C in 20 hours (55 percent yield), melted at 114°–115°C, and had a specific rotation of −24.8° (C = 2, in dioxane).

The N-carbobenzoxy-L-phenylalanine ester formed in the presence of benzylisonitrile in ethyl acetate at 70°C in 30 hours at 73 percent yield. M.P. 135°–137°C. $[\alpha]_D^{25} = -17.1$ (C = 2, in dioxane).

EXAMPLE 7

A solution of 6.0 g (20 mM) N-carbobenzoxy-L-phenylalanine, 3.3 g (24 mM) p-nitrophenol, and 1.6 g (24 mM) isopropyl isonitrile in 50 ml ethyl acetate was held at 60°C for 40 hours, and then evaporated. The residue was dissolved in ethanol, and the solution stored in a refrigerator until crystals formed. The crystals were filtered out, washed with petroleum ether, and dried. 4.5 g N-Carbobenzoxy-L-phenylalanine p-nitrophenyl ester was obtained (53 percent yield). M.P. 125.5°–127°C. $[\alpha]_D^{25} = -8.0°$ (C = 2.2, in chloroform).

Calculated for $C_{23}H_{20}N_2O_6$: 65.70% C; 4.80% H; 6.66% N. Found: 65.89% C; 4.83% H; 6.82% N.

p-Nitrophenol esters of other N-protected amino acids or peptides were formed in an analogous manner using partly different reaction conditions.

Thus, N-carbobenzoxy-S-benzyl-L-cysteine in ethyl acetate at 65°C gave the expected ester after 24 hours in a yield of 63 percent.

N-Tert-butyloxycarbonyl-L-alanine in methylene chloride was reacted at 40°C for 30 hours for a 52 percent yield of the nitrophenol ester.

Similarly, N-formyl-L-phenylalanine was esterified in dioxane at 70°C for 28 hours (48 percent yield).

The ester of N-carbobenzoxy-L-phenylalanyl-glycine was obtained in a yield of 56 percent after 24 hours in ethyl acetate at 65°C.

EXAMPLE 8

A solution of 5.02 g (20 mM) N-carbobenzoxy-L-valine, 5.61 g (20 mM) pentachlorophenol, and 2.0 g (30 mM) n-propyl isonitrile in 70 ml ethyl acetate was heated at 65°C for 24 hours. It was then stored in a refrigerator to precipitate crystals which were filtered out. A second crystal crop was obtained from the filtrate upon partial evaporation and recrystallized from petroleum ether and ethyl acetate. The combined yield of N-carbobenzoxy-L-valine pentachlorophenyl ester was 8.05 g (81 percent). It was reduced by recrystallizing from methanol to 6.8 g (68 percent). M.P. 142.5°–143.5°C. $[\alpha]_D^{25} = -20.2°$ (C = 0.49, in chloroform).

Calculated for $C_{19}H_{16}O_4NCl_5$: 45.67% C; 3.23% H; 2.80% N; 35.48% Cl. Found: 45.77% C; 3.26% H; 2.68% N; 35.76% Cl.

Other esters of pentachlorophenol were produced in an analogous manner. The ester of N-carbobenzoxy-L-phenylalanine was formed in the presence of isopropyl isonitrile in ethyl acetate at room temperature in 51 hours in a yield of 75 percent, and melted at 153°–156°C. $[\alpha]_D^{25} = -52.6°$ (C = 1, DMF [dimethylformamide]). The same ester, when prepared at 65°C in DMF in 24 hours, was obtained in a yield of 86 percent and melted at 154°–157°C. $[\alpha]_D^{25} = -52.0°$ (C = 1, in DMF).

The ester of $N^\alpha$, $N^\epsilon$-dicarbobenzoxy-L-lysine was formed in the presence of n-propyl isonitrile in ethyl acetate at 65°C in 24 hours in a yield of 90 percent. M.P. 154°–156°C. $[\alpha]_D^{25} = -7.8°$ (C = 0.8, in chloroform).

The N-carbobenzoxy-L-serine ester was obtained in the presence of tert-butyl isonitrile in a mixture of ethyl acetate and DMF at 50°C in 28 hours at 43 percent yield. M.P. 183°–186°C. $[\alpha]_D^{25} = -23.3°$ (C = 1, in DMF).

EXAMPLE 9

A solution of 6.0 (20 mM) N-carbobenzoxy-L-phenylalanine, 5.3 g (20 mM) pentachlorophenol, and 2.0 g (30 mM) is isopropyl isonitrile in 40 ml chloroform was mixed with a solution of 2.8 g (20 mM) glycine ethyl ester hydrochloride and 2.02 g (20 mM) triethylamine in 30 ml chloroform. The mixture was heated at 50°C for 24 hours and evaporated. The residue was taken up in 150 ml ethyl acetate. The solution was washed sequentially with 100 ml water, 120 ml 1-N hydrochloric acid, four times 120 ml 5% sodium bicarbonate solution, and again with 100 ml water, then dried with desiccated sodium sulfate and evaporated. When the residue was crystallized from ethyl acetate and petroleum ether, 6.3 g N-carbobenzoxy-L-phenylalanyl-glycine ethyl ester was obtained (82 percent yield). Recrystallizing from ethyl acetate and petroleum ether reduced the yield to 5.4 g (70%). M.P. 107°–108.5°C. $[\alpha]_D^{25} = -17.1°$ (C = 2, in ethanol).

Calculated for $C_{21}H_{24}O_5N_2$: 65.61% C; 6.29% H; 7.29% N. Found: 65.84% C; 6.41% H; 7.04% N.

EXAMPLE 10

Other peptide derivatives were produced by the method of Example 9 in the presence of isopropyl isonitrile and a compound having an active hydroxyl group from amino acids or oligopeptides in the molar proportions indicated in the above Example.

N-Carbobenzoxy-L-alanine was thus reacted with L-phenylalanine methyl ester in the presence of N-hydroxysuccinimide in ethyl acetate as the solvent medium at 45°C for 40 hours, and the expected peptide derivative was recovered in a yield of 65 percent.

N-Carbobenzoxy-S-benzyl-L-cysteine and glycine ethyl ether were reacted in chloroform at 60°C for 24 hours in the presence of p-nitrophenol with a yield of 81 percent.

N-Carbobenzoxy-glycine and L-phenylalanyl-glycine ethyl ester reacted with each other at room temperature in the presence of pentachlorophenol to give a yield of 73 percent in 48 hours.

The Examples do not exhaust the combinations and permutations of compounds and radicals which may be arrived at from these teachings in an obvious manner, and homologs and analogs may be substituted for the reactants and other ingredients specifically referred to above.

Acyl groups of organic acids other than formic, phthalic benzenesulfonic acid and its substitution products may be employed as masking agents replacing hydrogen in the amino groups of the N-protected amino acids, other amino acids may be employed, and the radicals protecting the carboxyl groups of the carboxylprotected amino acids may be other than the alkyl and benzyl radicals exemplified, although the latter, when replacing hydrogen in carboxyl, directly lead to active esters suitable for peptide synthesis, while the alkali metal salts and amides need to be converted to the esters in a second step. The choice of suitable isonitriles of the formula R-NC is limited only by the presence of functional groups R predictably interfering with the desired reaction, and of insignificant number when compared with the obviously operative isonitriles. The alkyls having 3 or 4 carbon atoms, benzyl, ethoxycarbonylmethyl, and phenyl have been chosen for R in the above formula for the sake of illustration only.

What is claimed is:

1. A method of producing a peptide which comprises contacting a first compound having an amino group masked by a masking group conventional in peptide chemistry and an available carboxyl group with a second compound having a carboxyl group masked by a masking group conventional in peptide chemistry and an available amino group in a liquid reaction medium including an amount of an isonitrile effective for causing formation of a peptide by condensation of the available amino and carboxyl groups of said first and second compounds, said compounds being members of the group consisting of amino acids and oligopeptides, and being contacted until said peptide is formed as a reaction product.

2. A method as set forth in claim 1, wherein the masking group masking the amino group of said first compound is carboalkoxy having up to five carbon atoms or carbobenzoxy.

3. A method as set forth in claim 2, wherein the carboxyl group of said second compound is masked as an alkyl ester having up to four carbon atoms in said alkyl, as an alkali metal salt, or as an amide.

4. A method as set forth in claim 1, one of said compounds being a dipeptide constituted by two amino acid units.

5. A method as set forth in claim 1, said reaction medium having a temperature of 10° to 80°C, said second compounds being contacted with said first compound in an approximately equimolecular amount, and said amount of said isonitrile being at least equimolecular to the amount of said first compound.

6. A method as set forth in claim 5, said isonitrile being of the formula R-NC, wherein R is alkyl having 3 or 4 carbon atoms, allyl, benzyl, phenyl, or ethoxycarbonylmethyl.

7. A method as set forth in claim 6, said amino group of said first compound being masked by a member of the group consisting of carbobenzoxy, tert-butyloxycarbonyl, phthalyl, formyl, tosyl, p-nitrobenzyloxycarbonyl, p-methoxybenzyloxycarbonyl, tert-amyloxycarbonyl, trityl, trimethylsilyl, benzenesulfonyl, and o-nitrophenylsulfonyl.

8. A method as set forth in claim 7, wherein the carboxyl group of said second compound is masked as an alkyl ester having up to four carbon atoms in said alkyl or as a benzyl ester.

9. A method as set forth in claim 8, said compound being selected from the group consisting of arginine, alanine, aspartic acid, cysteine, glycine, glutamic acid, lysine, phenylalanine, phenylalanyglycine, proline, serine, and valine.

10. A method as set forth in claim 1, which further comprises recovering said reaction product.

11. A method as set forth in claim 1, wherein said first and second compounds are contacted in said medium in the presence of a third compound having an active hydroxyl group, said third compound being a member of the group consisting of nitrophenol, trichlorophenol, tetrachlorophenol, pentachlorophenol, 8-hydroxyquinoline, and the N-hydroxy derivatives of succinimide, benzotriazole, and piperidine, the amount of said third compound being sufficient to increase the yield of said peptide over the yield of said peptide obtained in the absence of said third compound.

* * * * *